US010117621B2

(12) United States Patent
Berger et al.

(10) Patent No.: US 10,117,621 B2
(45) Date of Patent: Nov. 6, 2018

(54) IMPLANTABLE DEVICE AND IMPLANTABLE SYSTEM COMPRISING THE SAME

(71) Applicant: Infineon Technologies AG, Neubiberg (DE)

(72) Inventors: Jan Berger, Villach (AT); Bernhard Wedl, Graz (AT); Dirk Hammerschmidt, Villach (AT); Walther Pachler, Graz (AT); Horst Theuss, Wenzenbach (DE); Harald Witschnig, Landskron (AT)

(73) Assignee: Infineon Technologies AG, Neubiberg (DE)

( * ) Notice: Subject to any disclaimer, the term of this patent is extended or adjusted under 35 U.S.C. 154(b) by 230 days.

(21) Appl. No.: 15/141,996

(22) Filed: Apr. 29, 2016

(65) Prior Publication Data

US 2016/0317095 A1 Nov. 3, 2016

(30) Foreign Application Priority Data

Apr. 30, 2015 (DE) ........................ 10 2015 106 810

(51) Int. Cl.
| | |
|---|---|
| *A61B 5/00* | (2006.01) |
| *A61B 5/0205* | (2006.01) |
| *A61B 5/145* | (2006.01) |
| *A61B 5/026* | (2006.01) |
| *A61B 5/024* | (2006.01) |
| *A61B 5/05* | (2006.01) |
| *A61B 5/01* | (2006.01) |
| *A61B 5/0215* | (2006.01) |

(52) U.S. Cl.
CPC .......... *A61B 5/6862* (2013.01); *A61B 5/0215* (2013.01); *A61B 5/02444* (2013.01); *A61B 2560/0214* (2013.01)

(58) Field of Classification Search
None
See application file for complete search history.

(56) References Cited

U.S. PATENT DOCUMENTS

| 3,149,492 | A | 9/1964 | Weinberg |
| 6,015,387 | A | 1/2000 | Schwartz et al. |
| 7,468,039 | B2 * | 12/2008 | Lui ................. A61B 5/0261 128/100.1 |
| 9,775,991 | B1 * | 10/2017 | Hakki ................. A61N 1/057 |
| 2008/0171023 | A1 | 7/2008 | Boles et al. |

(Continued)

FOREIGN PATENT DOCUMENTS

DE   102012022032 A1   5/2014

*Primary Examiner* — Brian T Gedeon
(74) *Attorney, Agent, or Firm* — Eschweiler & Potashnik, LLC

(57) ABSTRACT

An implantable device includes a body part and a piezoelectric part. The body part is configured to grasp a pulsatile organic or inorganic tissue. The piezoelectric part is mechanically coupled to the body part and is configured to convert a varying shear force transferred from the body part to the piezoelectric part into voltage. An implantable system, comprises the implantable device and a stent like object configured to be inserted and deployed within a pulsatile or static tissue. The implantable device is configured to form a sealed junction with the pulsatile tissue while pressing against an outer circumference area of the stent.

18 Claims, 15 Drawing Sheets

(56) References Cited

U.S. PATENT DOCUMENTS

| | | | |
|---|---|---|---|
| 2009/0212645 A1* | 8/2009 | Theuss | H02K 35/02 |
| | | | 310/15 |
| 2010/0171394 A1* | 7/2010 | Glenn | A61N 1/372 |
| | | | 310/339 |
| 2010/0298720 A1* | 11/2010 | Potkay | A61B 5/0215 |
| | | | 600/485 |
| 2013/0150685 A1 | 6/2013 | Toth | |

* cited by examiner

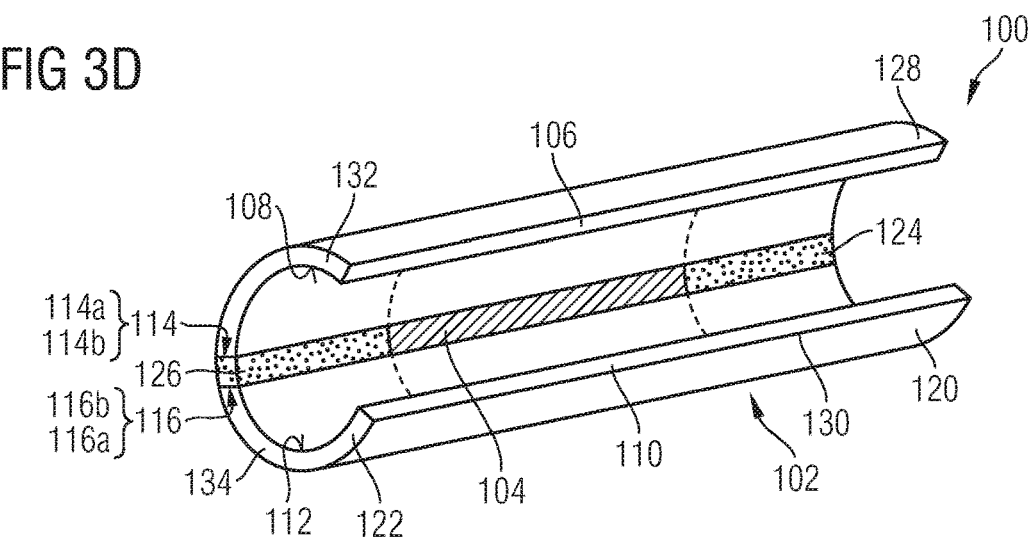
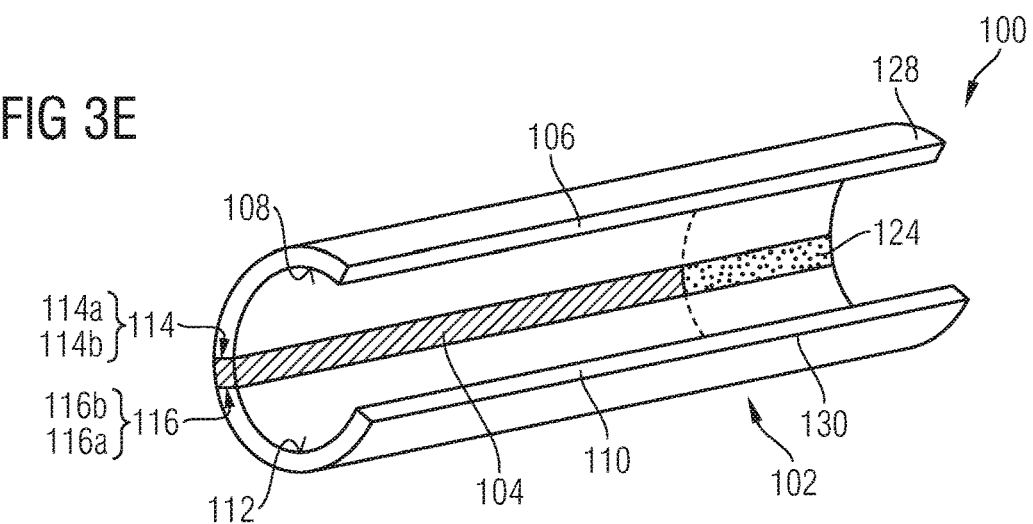
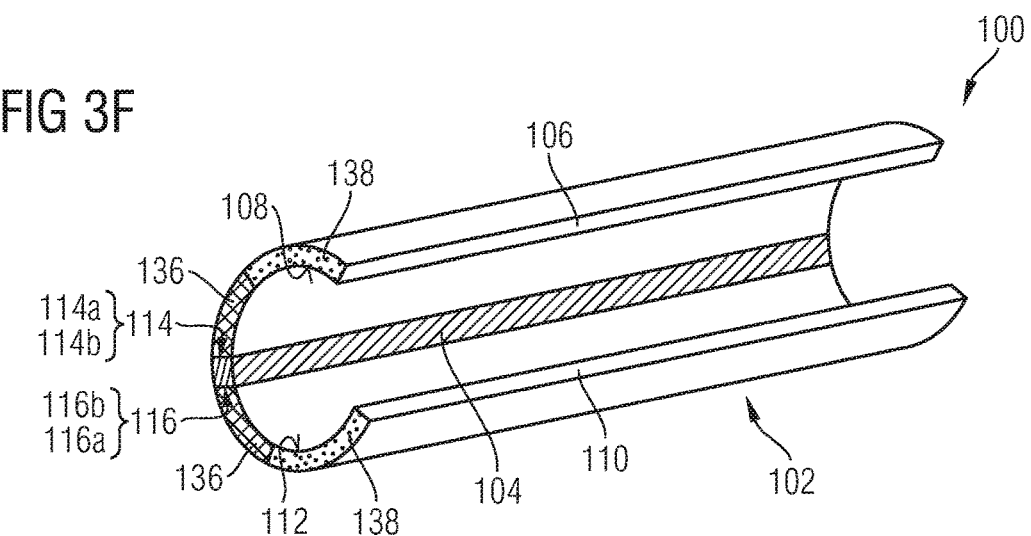

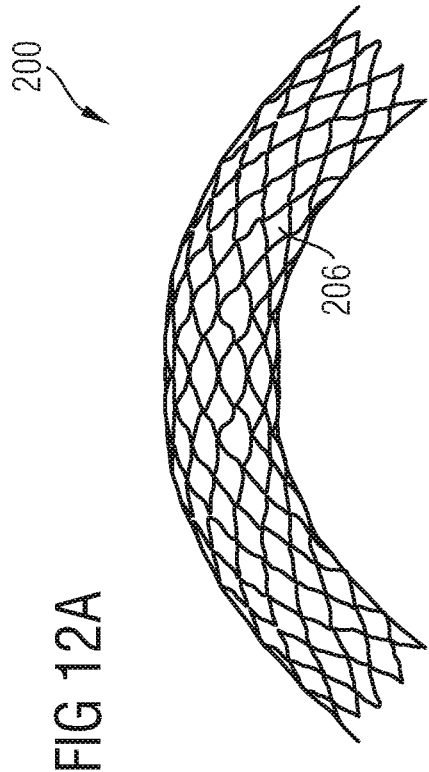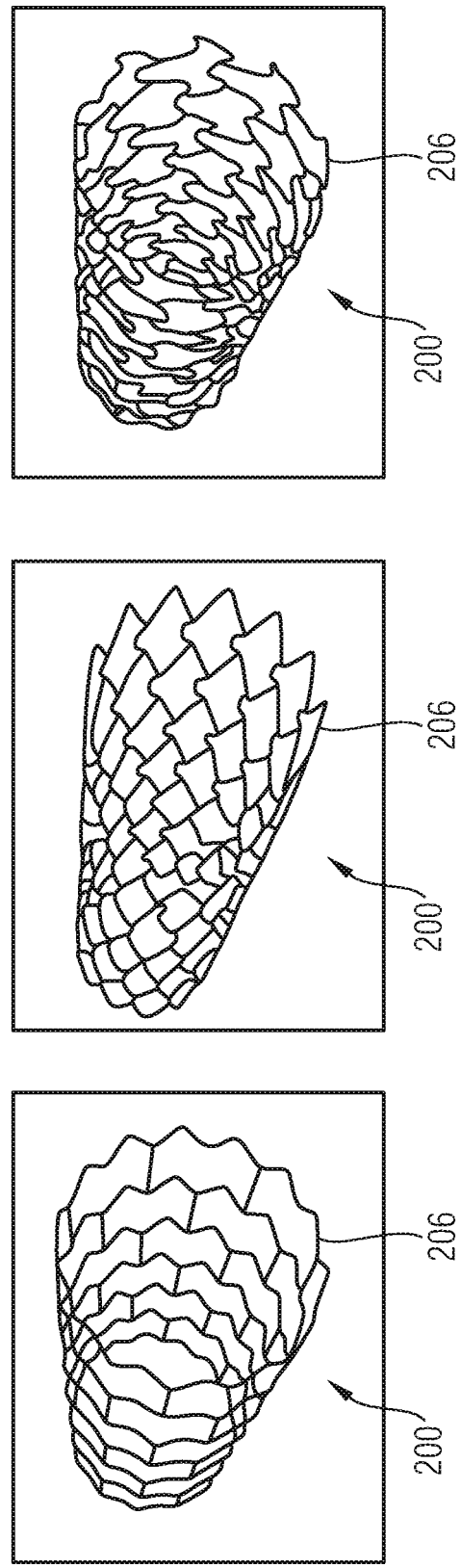

206

206

206

206

206

206

206

206

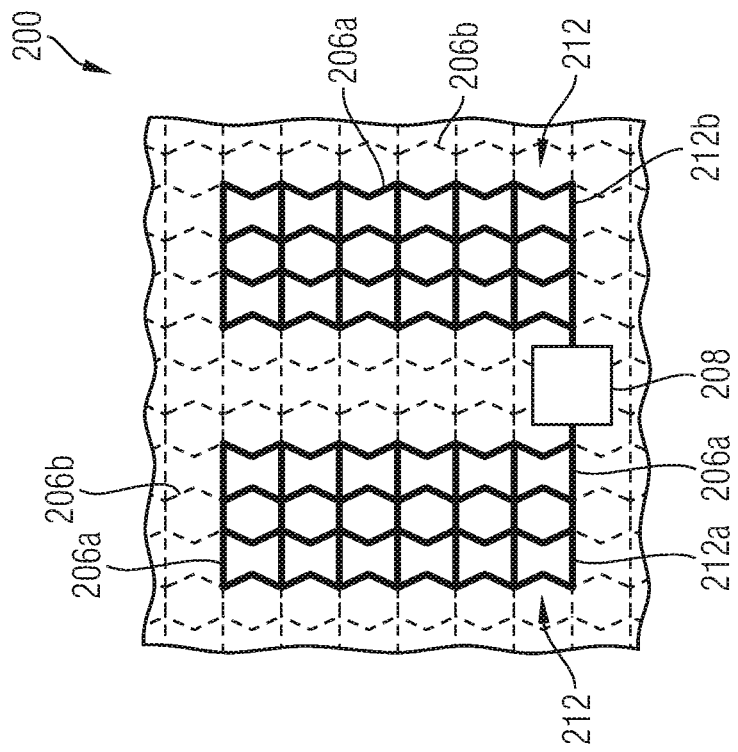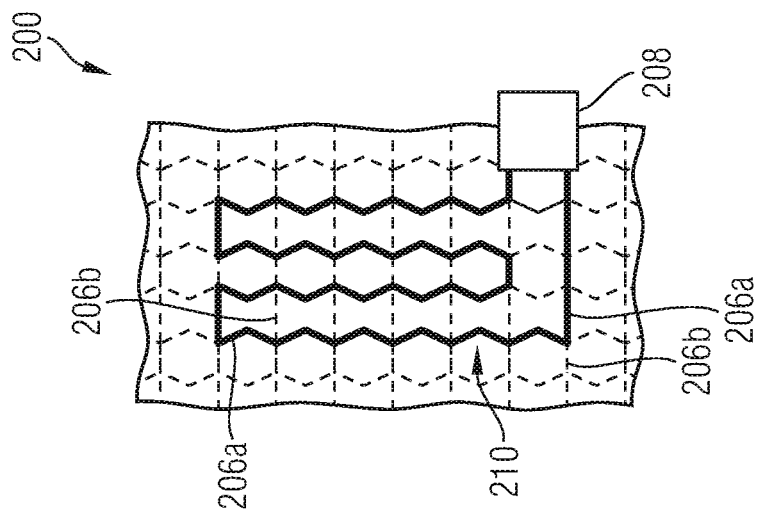

IMPLANTABLE DEVICE AND IMPLANTABLE SYSTEM COMPRISING THE SAME

CROSS REFERENCE TO RELATED APPLICATION

This application claims priority to German Patent Application number 102 015 106 810.9 filed Apr. 30, 2015, which is hereby incorporated by reference in its entirety.

BACKGROUND

Implantable biosensors for monitoring health have witnessed rapid developments in the past decade. While innovations in microelectronics enabled continuous miniaturization of sensing devices, battery technology became a limiting factor. For this reason research in energy harvesting systems has increased drastically. Today the leading energy harvesting technologies are piezoelectric, thermoelectric, electromagnetic movement, biocatalytic fuel cells, photovoltaic, radio frequency. It is desirable to improve the efficiency of energy harvesting properties of these implantable biosensors or implantable devices.

SUMMARY

The present disclosure provides an implantable device providing an increased efficiency in harvesting or measuring tissue pulsation and being easy to implant.

According to an embodiment of an implantable device, the implantable device comprises a body part and a piezoelectric part. The body part is adapted to grasp a pulsatile tissue. The piezoelectric part is mechanically coupled to the body part and is adapted to convert a varying shear force transferred from the body part to the piezoelectric part into voltage.

According to an embodiment of an implantable system, the implantable system comprises the implantable device and a stent adapted to be inserted and deployed within a pulsatile tissue. The implantable device is adapted to form a sealed junction with the pulsatile tissue while pressing against an outer circumference area of the stent.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of the invention and are incorporated in and constitute a part of this specification. The drawings illustrate the embodiments of the present invention and together with the description serve to explain principles of the invention. Other embodiments of the invention and intended advantages will be readily appreciated as they become better understood by reference to the following detailed description.

FIGS. 3A to 3F are schematic perspective views of an implantable device according to different embodiments.

FIGS. 12A to 12D are schematic perspective views of a stent according to different embodiments.

FIGS. 14A and 14B illustrate different antenna structures of a stent according to different embodiments.

DETAILED DESCRIPTION

In the following detailed description, reference is made to the accompanying drawings, which form a part hereof, and in which are shown by way of illustrations specific embodiments in which the invention may be practiced. It is to be understood that other embodiments may be utilized and structural or logical changes may be made without departing from the scope of the present invention. For example, features illustrated or described for one embodiment can be used on or in conjunction with other embodiments to yield yet a further embodiment. It is intended that the present invention includes such modifications and variations. The examples are described using specific language which should not be construed as limiting the scope of the appending claims. The drawings are not scaled and are for illustrative purposes only. For clarity, the same elements have been designated by corresponding references in the different drawings if not stated otherwise.

The terms "having", "containing", "including", "comprising" and the like are open and the terms indicate the presence of stated structures, elements or features but not preclude additional elements or features. The articles "a", "an" and "the" are intended to include the plural as well as the singular, unless the context clearly indicates otherwise.

The term "electrically connected" describes a permanent low-ohmic connection between electrically connected elements, for example a direct contact between the concerned elements or a low-ohmic connection via a metal and/or highly doped semiconductor. The term "electrically coupled" includes that one or more intervening element(s) adapted for signal transmission may be provided between the electrically coupled elements, for example resistors, resistive elements or elements that are controllable to temporarily provide a low-ohmic connection in a first state and a high-ohmic electric decoupling in a second state.

Figure 1A:
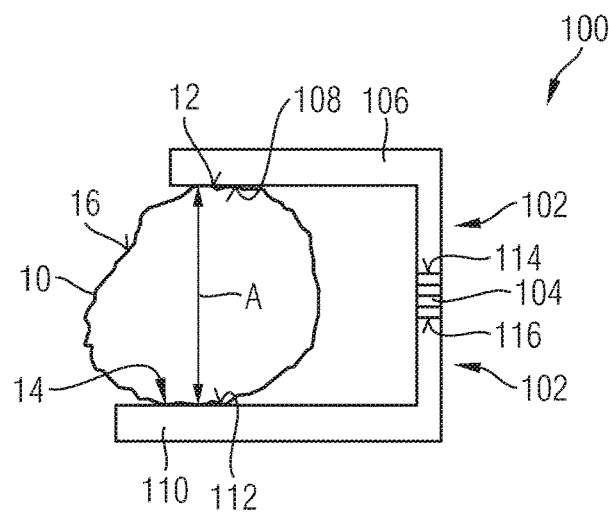
FIG. 1A is a schematic view of an implantable device according to an embodiment at a contracted state of a pulsatile tissue.

FIG. 1A is a schematic view of an implantable device 100 according to an embodiment at a contracted state of a pulsatile tissue 10.

The implantable device 100 comprises a body part 102 and a piezoelectric part 104. The body part 102 is adapted to grasp the pulsatile tissue 10. The piezoelectric part is mechanically coupled to the body part 102 and is further adapted to convert a varying shear force F transferred from the body part 102 to the piezoelectric part 104 into voltage. The body part 102 comprises a first grasping part 106 being adapted to grasp a first tissue part 12 of the pulsatile tissue 10 with a first surface area 108, and a second grasping part 110 being adapted to grasp a second tissue part 14 of the pulsatile tissue 10 with a second surface area 112. The first surface area 108 and the second surface area 112 face each other, to enclose the pulsatile tissue 10, wherein the first tissue part 12 directly abuts the first surface area 108 of the first grasping part 106 and the second tissue part 14 directly abuts the second surface area 112 of the second grasping part 110. The piezoelectric part 104 is mechanically interconnected between the first grasping part 106 and the second grasping part 110.

Figure 1B:
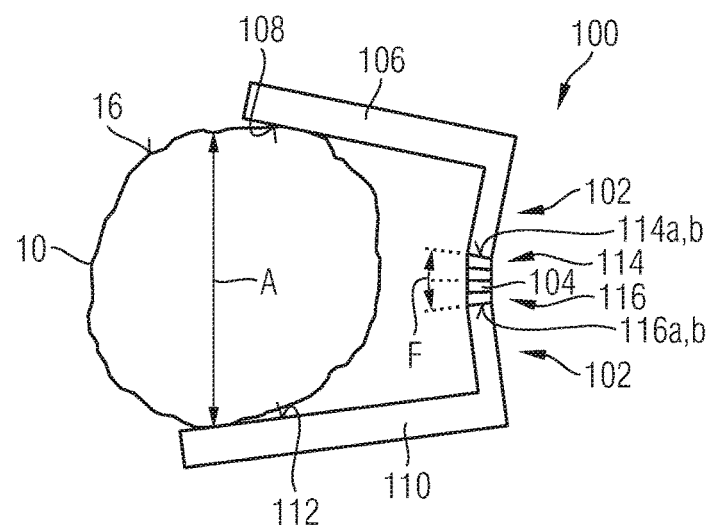
FIG. 1B is a schematic view of an implantable device according to an embodiment at an expanded state of a pulsatile tissue.

As can be seen from the comparison of FIGS. 1A and 1B, the pulsatile tissue 10 performs a reciprocal contraction and expansion within at least a direction A being substantially orthogonal or orthogonal to the first surface area 108 of the first grasping part 106 and the second surface area 112 of the second grasping part 110. The pulsatile tissue 10 may be a blood vessel or any other organic or inorganic vessel in a human body or an animal body or an object in general which performs a pulsatile movement. In case no pulsatile movement of the tissue 10 should be necessary, it is also possible to employ an organic or inorganic vessel/tube like object, which is an a static state. In an embodiment, the pulsatile tissue 10 may also be a part of a muscle. Any pulsatile tissue 10 may be employed for harvesting or movement measurement by the implantable device 100, in case the pulsatile tissue 10 is adapted to transfer a shear force on the first grasping part 106 and the second grasping part 110 enclosing the pulsatile tissue 10.

As can be seen from FIG. 1B, the expansion of the pulsatile tissue 10 presses the first grasping part 106 and the second grasping part 110 apart from each other. The first grasping part 106 is mechanically connected to the piezoelectric part 104 at a first interface area 114. The second grasping part 110 is mechanically connected with the piezoelectric part 104 at a second interface area 116. At the first interface area 114, a boundary surface 114a of the first grasping part 106 faces a boundary surface 114b of the piezoelectric part 104. At the second interface area 116, a boundary surface 116a of the second grasping part 110 faces a boundary surface 116b of the piezoelectric part 104.

According to an embodiment, the first grasping part 106 is formed such that the orientations of the first surface area 108 and the boundary surface 114b of the piezoelectric part 104 are fixed to each other. In addition, the second grasping part 110 may be formed such that the orientations of the second surface area 112 and the boundary surface 116b of the piezoelectric part 104 are fixed to each other. According to an embodiment, the first surface area 108 and the boundary surface 114b of the piezoelectric part 104 are parallel to each other. In addition, the second surface area 112 and the boundary surface 116b of the piezoelectric part 104 may be parallel to each other. The first grasping part 106 and the second grasping part 110 may be mechanically connected to the piezoelectric part 104 by gluing or mechanically fixing, for example.

Thus, in case of an expansion of the pulsatile tissue 10, as can be seen from FIG. 1B, the first grasping part 106 and the second grasping part 110 generate, comparable to a scissor, a shear force acting on the boundary surfaces 114b and 116b of the piezoelectric part 104 and thus on the body or bulk of the piezoelectric part 104 between its boundary surfaces 114b and 116b. In other words, the part of the piezoelectric part 104 facing the pulsatile tissue 10 is expanded, wherein the part of the piezoelectric part 104 lying opposite to the pulsatile tissue 10 is contracted, when the pulsatile tissue 10 is expanded. Due to the varying shear force F within the piezoelectric part 104, a piezoelectric voltage is generated, which may be harvested by the implantable device 100 or also measured by the implantable device to sense the movement of the pulsatile tissue 10.

Due to the transfer of a shear force F from the first and second grasping parts 106, 110 to the piezoelectric part 104, a piezoelectric force may be generated by employing high leverage forces on the boundary surfaces 114b and 116b of the piezoelectric part 104 from the first and second surface areas 108 and 112 of the first and second grasping parts 106 and 110, respectively. Thus, the efficiency in harvesting or measuring a tissue pulsation of the pulsatile tissue 10 may be increased while the implantable device 100 is easy to be implanted.

Figure 2:
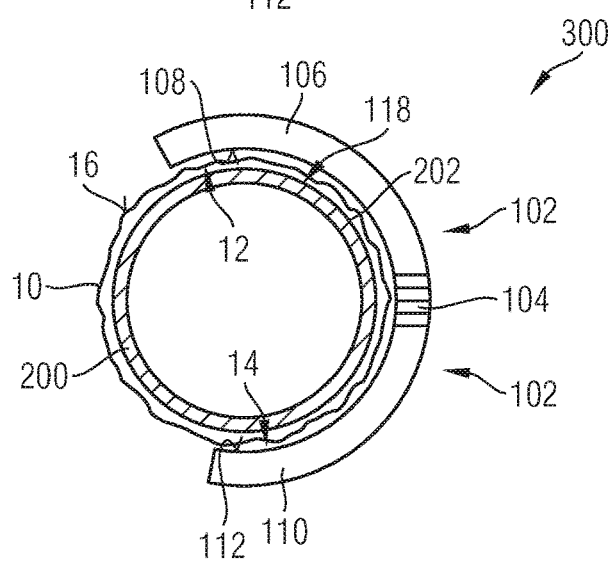
FIG. 2 is a schematic view of an implantable system according to an embodiment.

FIG. 2 is a schematic view of an implantable system 300 according to an embodiment.

The implantable system 300 comprises the implantable device 100 and further comprises a stent 200, which is adapted to be inserted and deployed within the pulsatile tissue 10. In case of the implantable system 300 the vessel/tube like object holding the stent can also be us in non-pulsatile operation. In other words, the features of the implantable system 300 are not restricted to the embodiment of harvesting mechanical energy from a pulsatile tissue 10. The implantable device 100 is adapted to form a sealed junction area 118 with the pulsatile tissue 10 while pressing against an outer circumferential area of an circumferential surface 202 of the stent 200. According to an embodiment, the implantable device 100 may be formed as a cuff to enclose at least a part of the pulsatile tissue 10. The stent 200 may be a mesh tube inserted into a natural passage or conduit in a human or animal body to prevent or counteract a disease-induced, localized flow constriction. The stent 200 may also be a tube-formed device used to temporally or permanently hold such a natural conduit open. An example for a temporally application is the provision for access in a surgery operation. The stent 200 may also comprise some electronic functionality or sensor functionality, as will be described later.

FIGS. 3A to 3F are schematic perspective views of an implantable device 100 according to different embodiments. As can be seen from FIGS. 3A to 3F, the implantable device 100 may be formed as a cuff which may be wrapped around the circumferential surface 16 of the pulsatile tissue 10. For better illustrating the properties and structures of the implantable device 100, the pulsatile tissue 10 is not shown in FIGS. 3A to 3F. An illustration of an implantable device 100 grasping the pulsatile tissue 10 can be found in FIG. 2, wherein the provision of the stent 200 is optional and may be employed according to an embodiment.

As can be seen from FIGS. 3A to 3F, the body part 102 and the piezoelectric part 104 may form a cuff adapted to grasp the pulsatile tissue 10. As can be seen from FIGS. 3A to 3C, the piezoelectric part 104 is mechanically interconnected between the first grasping part 106 and the second grasping part 110.

Figure 3A:
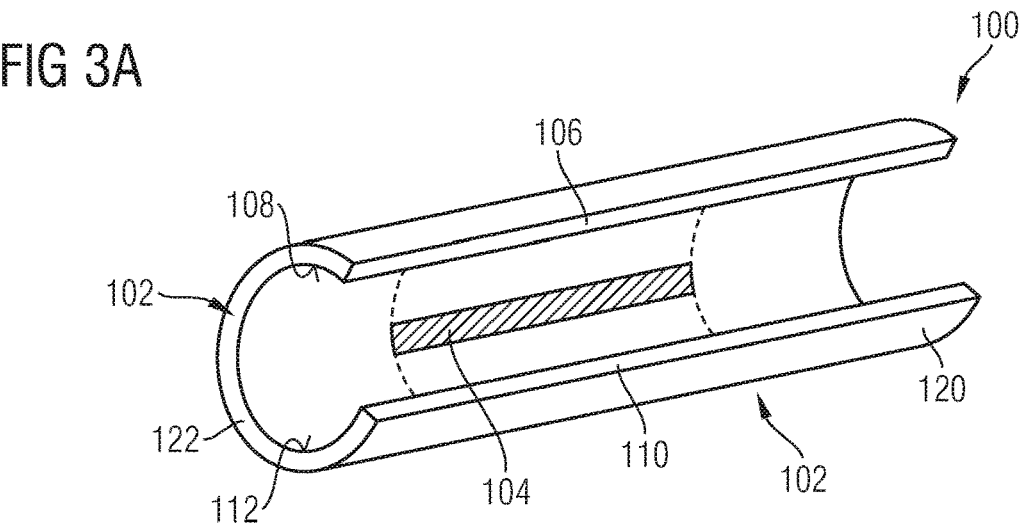

According to an embodiment of FIG. 3A, the piezoelectric part 104, the first grasping part 106 and the second grasping part 110 may be arranged in a middle part of the body part 102, wherein the piezoelectric part 104, the first grasping part 106 and the second grasping part 110 are neighboured by a first end part 120 and a second end part 122 of the body part 102. The first end part 120 and the second end part 122 may be formed as a cuff and may be integrally formed with the first grasping part 106 and the second grasping part 110.

Figure 3B:
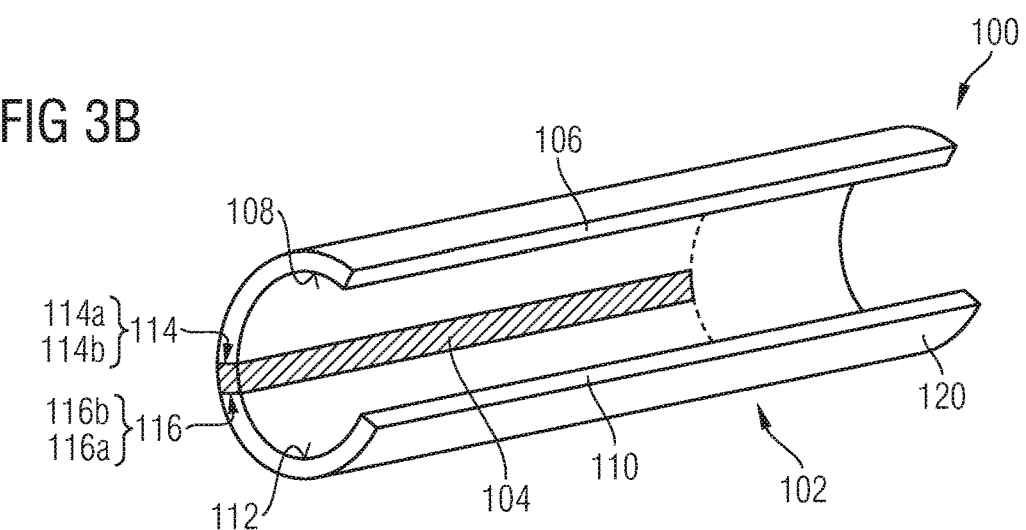

As can be seen from FIG. 3B, according to an embodiment, the piezoelectric part 104, the first grasping part 106 and the second grasping part 110 may be extended to one end of the body part 102 and are neighboured by the first end part 120 only. According to the embodiments of FIGS. 3A and 3B, the first grasping part 106 and the second grasping part 110 are mechanically connected with each other by the interconnected piezoelectric part 104 and at least one end part 120, 122 of the body part 102.

Figure 3C:
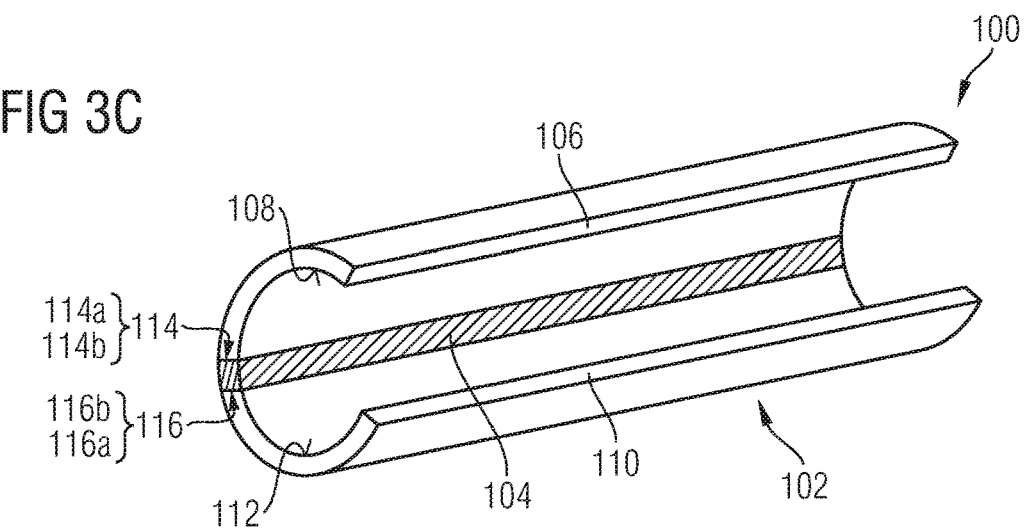

According to an embodiment of FIG. 3C, the piezoelectric part 104, the first grasping part 106 and the second grasping part 110 are extended from one end to the other end of the body part 102 of the implantable device 100. Thus, the first grasping part 106 and the second grasping part 110 are mechanically connected with each other by the interconnected piezoelectric part 104 only.

As can be seen from FIGS. 3D and 3E, the first end part 120 and/or the second end part 122 of the body part 102 may comprise an elastic end part 124, 126. The elastic end part 124 of the first end part 120 is mechanically interconnected between a first grasping end part 128 and a second grasping end part 130. The elastic end part 126 of the second end part 122 is mechanically interconnected between a first grasping end part 132 and a second grasping end part 134 of the second end part 122. In case the first grasping end parts 128, 132 are formed integrally with the first grasping part 106 (and in case the second grasping end parts 130, 134 are integrally formed with the second grasping part 110), the elastic end part 124 (or the elastic end parts 124, 126) ensures that the shear force F is focussed on the piezoelectric part 104 and not absorbed by the first end part 120 (or by the end parts 120, 122). Thus, according to the embodiment of FIGS. 3D and 3E, the first grasping part 106 and the second grasping part 110 may be mechanically connected with each other by the interconnected piezoelectric part 104 and at least one end part 120, 122 comprising an elastic end part 124, 126. According to another embodiment, the body part 102 may also comprise a piezoelectric material. The elastic end part 124, 126 may comprise an elastic material (having an elastic module of lower than 1 kN/mm$^2$), wherein the first grasping part 106, the second grasping part 110, the first grasping end parts 128, 132 and the second grasping end parts 130, 134 may comprise a stiff or rigid material (having an elastic module of higher than 1 kN/mm$^2$) and/or an elastic or flexible material. The elastic end parts 124, 126 may comprise a flexible or elastic material such as a synthetic material comprising PET, PI, or silicone. According to an embodiment, a region of the first grasping part 106 and of the second grasping part 110 directly adjoining the piezoelectric part 104 comprises a stiff material.

As can be seen from FIG. 3F, the first grasping part and the second grasping part 110 may comprise a stiff part 136. The stiff part 136 may comprise, for example, a rigid or stiff material such as glass, metal (e.g. titanium), silicon, or a biocompatible material. The elastic part 138 may comprise a synthetic material. The synthetic material may comprise PET, PI, or silicone. The stiff part 136 and the elastic part 138 may comprise a synthetic material of the same material composition, wherein the synthetic material is chemically hardened within the stiff part 136. The stiff part 136 and the elastic part 138 may, according to another embodiment, comprise a synthetic material of the same material composition, wherein the synthetic material is coated with a rigid material within the stiff part 136. The stiff part 136 and the elastic part 138 may also comprise different materials and may be mechanically connected by means of gluing or welding, for example.

Due to the provision of a stiff part 136 and an elastic part 138, the cuff-formed implantable device 100 may be easily wrapped around the pulsatile tissue 10 by deforming the elastic part 138, while a pulsatile reciprocal movement, i.e. an expansion and contraction of the pulsatile tissue 10 presses the stiff parts 136 of the first grasping part 106 and the second grasping part 110 apart, to transfer a shear force F from the stiff parts 136 into the piezoelectric part 104. According to an embodiment, the first surface area 108 and the second surface area 112 are within the stiff parts 136 of the first grasping part 106 and the second grasping part 110, respectively. Thus, an optimized transfer of the force of the pulsatile tissue 10 in the direction A to the piezoelectric part 104 may be achieved.

Figure 4A:
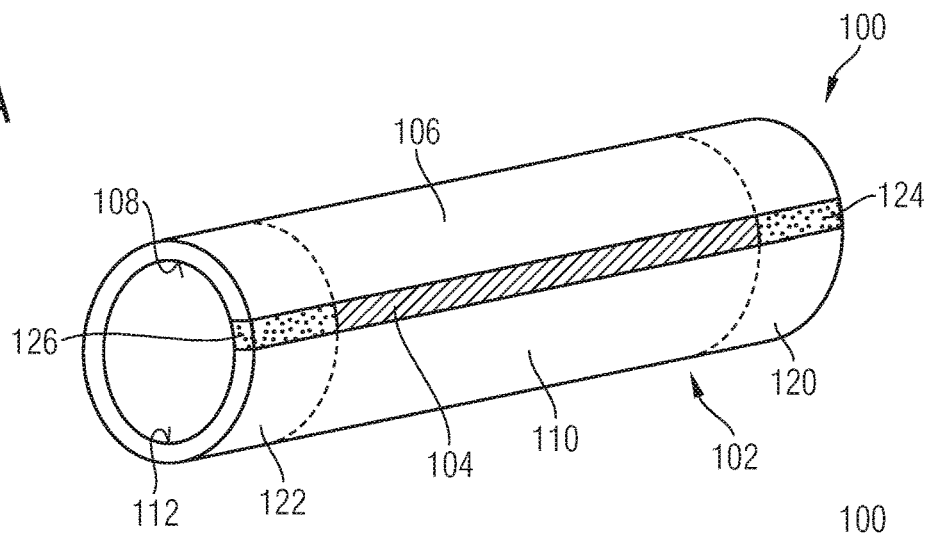
FIGS. 4A to 4C are schematic perspective views of an implantable device according to further different embodiments.
Figure 4B:
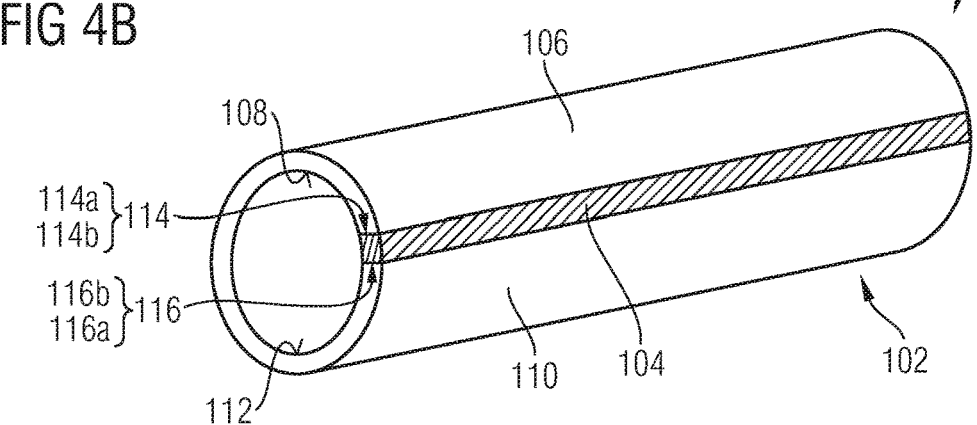
Figure 4C:
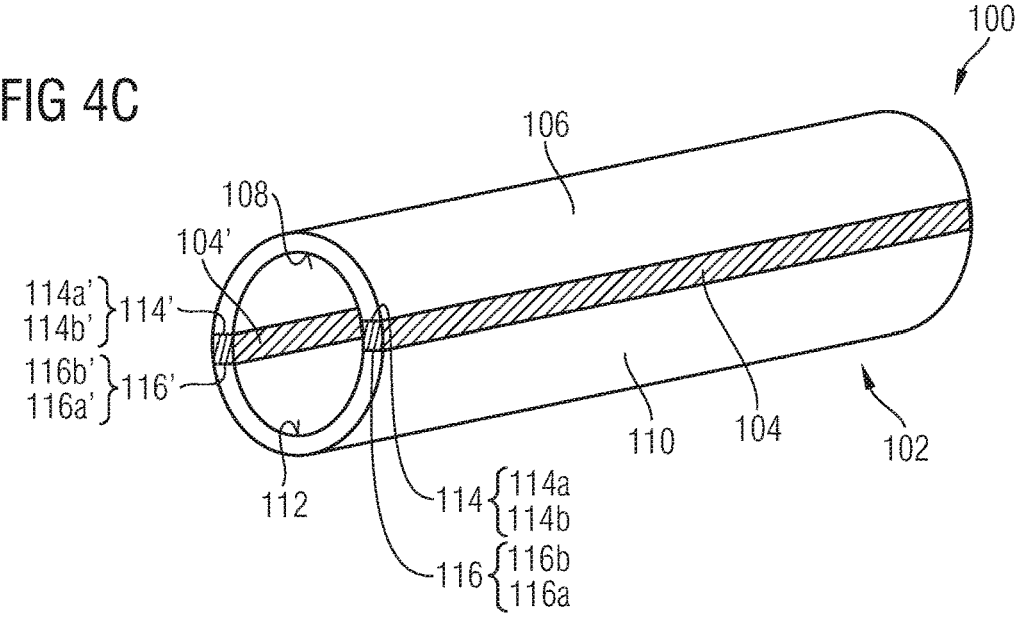

FIGS. 4A to 4C are schematic perspective views of an implantable device 100 according to further different embodiments. As can be seen from FIGS. 4A to 4C, the body part 102 and the piezoelectric part 104 form a tube structure adapted to enclose the pulsatile tissue 10.

According to the embodiment of FIG. 4A, a first end part 120 comprising an elastic end part 124 and a second end part 122 comprising an elastic end part 126 are provided to be neighboured to the piezoelectric part 104, the first grasping part 106 and the second grasping part 110.

According to the embodiment of FIG. 4B, the piezoelectric part 104, the first grasping part 106 and the second grasping part 110 are extended from a first end to a second end of the body part 102 of the implantable device.

According to the embodiment of FIG. 4C, an additional piezoelectric part 104' is mechanically interconnected between the first grasping part 106 and the second grasping part 110. Herein, the first grasping part 106 is mechanically connected to the additional piezoelectric part 104' at a first interface area 114'. The second grasping part 110 is mechanically connected with the additional piezoelectric part 104' at a second interface area 116'. At the first interface area 114', a boundary surface 114*a*' of the first grasping part 106 faces a boundary surface 114*b*' of the additional piezoelectric part 104'. At the second interface area 116', a boundary surface 116*a*' of the second grasping part 110 faces a boundary surface 116*b*' of the additional piezoelectric part 104'. The shear force from the pulsatile tissue 10 may be transferred into the additional piezoelectric part 104' in an analogous way as into the piezoelectric part 104.

Figure 5A:
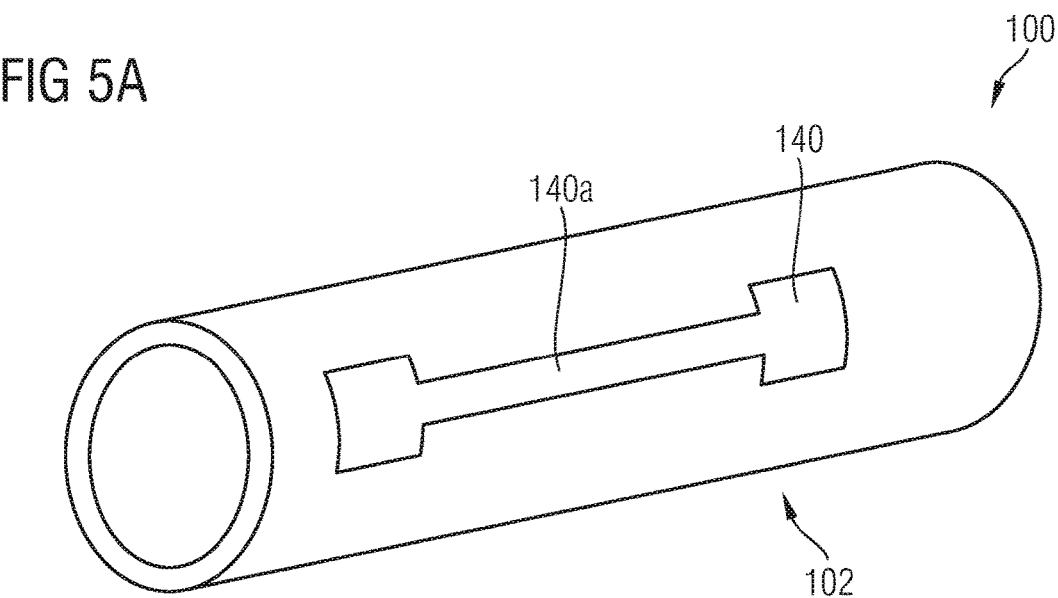
FIGS. 5A and 5B are schematic perspective views of an implantable device comprising an antenna structure according to different embodiments.
Figure 5B:
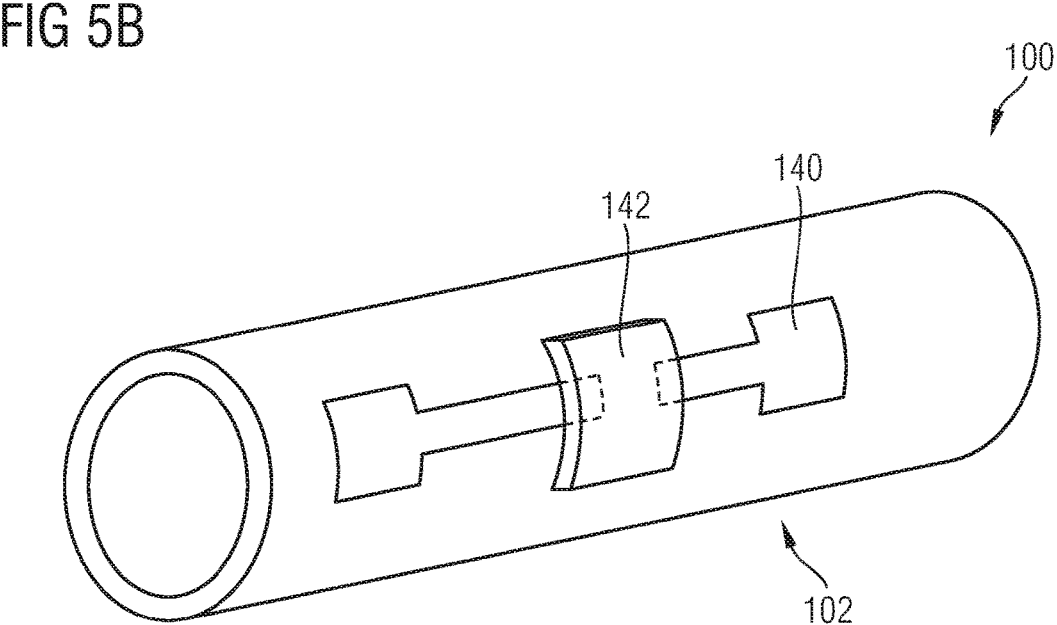

FIGS. 5A and 5B are schematic perspective views of an implantable device 100 comprising an antenna structure 140 according to different embodiments. Although not shown in the further drawings, the structure of the implantable device 100 may comprise the features as shown in FIG. 3A to 3F and FIG. 4A to 4C.

As can be seen from FIG. 5A, the implantable device 100 may have a tube structure with integrated electronic functionality for use in medical applications. The tube may be intended for implementation, e.g. by surgery, inside or outside of natural passages/conduits in the body of a human or an animal. Material of the body part 102 may be a biocompatible material formed of an elastic material or a stiff material as mentioned above. The implantable device 100 may also be coated with a passivation layer such as parylene in order make the implantable device 100 biocompatible. The base material of the body part 102 can either be conductive, e.g. metals or composite materials, also metals with an additional coating for passivation and/or isolation purposes, as well as non-polymers such as dielectric material, e.g. polylactate may be used. The material of the body part may further be porous or exhibit a mesh or sieve-like structure.

As can be seen from FIG. 5A, the implantable device 100 may be selectively coated on the inside and/or outside with a metal layer 140a to form an antenna structure 140. According to an embodiment, another passivation coating may be provided in order to electrically isolate the metal layer 140a from the environment. Thus, the implantable device 100 is formed as a tube-like structure with a selective metal layer 140a inside and/or outside of the tube-like structure to provide an antenna structure 140. As can be seen from FIG. 5B, the metal layer 140a may be connected to an additional electrical circuitry 142. The electrical circuitry 142 may comprise a semiconductor chip or flexible polymer electronics, such as printed polymer electronics.

Figure 6:
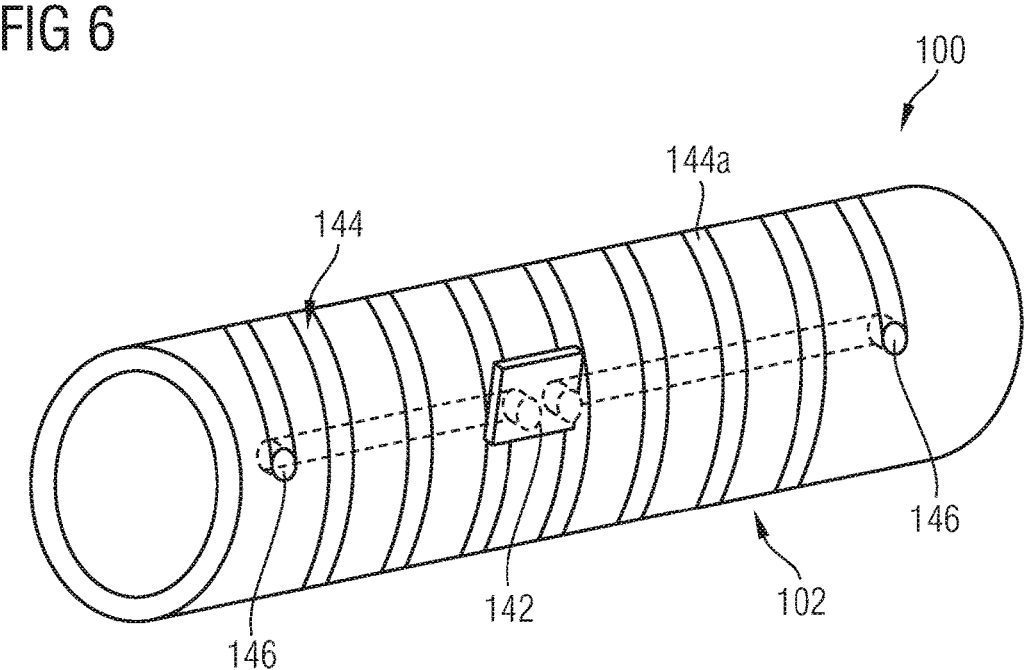
FIG. 6 is a schematic perspective view of an implantable device comprising an inductive structure according to an embodiment.

FIG. 6 is a schematic perspective view of an implantable device 100 comprising an inductive structure 144 according to an embodiment. As can be seen from FIG. 6, the implantable device 100 may comprise a tube structure including multiple layers of a metal and/or a non-conductive coating. According to the embodiment of FIG. 6, conductor lines of a metal layer 144a of an inductive structure 144 in adjacent layers can be electrically interconnected by through holes 146 in the body part 102 to be connected to an electrical circuitry 142 at an inside portion of the implantable device 100. Thus, the implantable device 100 having a tube-structure or a cuff-structure may be designed similar to a multilayer printed circuit board.

According to the embodiment of FIG. 6, a two layer metal plating comprising the metal layer 144a on the inside and on the outside surface of the body part 102 having a tube structure is provided to form a functionalized implantable device 100. The implantable device 100 may contain the electrical circuitry 142 such as a semiconductor chip or passive components, which may be either mounted onto the inner or outer surface of the implantable device 100. In case the implantable device is formed as a multilayer tube structure, these components might as well be implemented or embedded into different layers. As can be seen from the embodiment of FIG. 6, one dielectric layer and two metal layers are provided to form a functionalized implantable device 100. The components of the electrical circuitry 142 are, according to an embodiment, connected to the metal layer 140a or 144a, as can be seen from FIG. 5A, 5B and FIG. 6. The electrical circuitry 142 may also be manufactured by polymer electronics, i.e. by using electronic circuit structures on a polymer. The components of the electrical circuitry 142 may thus be rigid (including silicon chips) or flexible (using polymer electronics). According to FIGS. 5A and 5B, the metal layer 140a is an antenna or contains an antenna, wherein in the embodiment of FIG. 6, the metal layer 144a contains an inductance.

Thus, the implantable device 100 may further comprise an antenna structure 140 or an inductive structure 144 coated on the surface of the body part 102 by a metal layer 140a or 144a.

Figure 7:
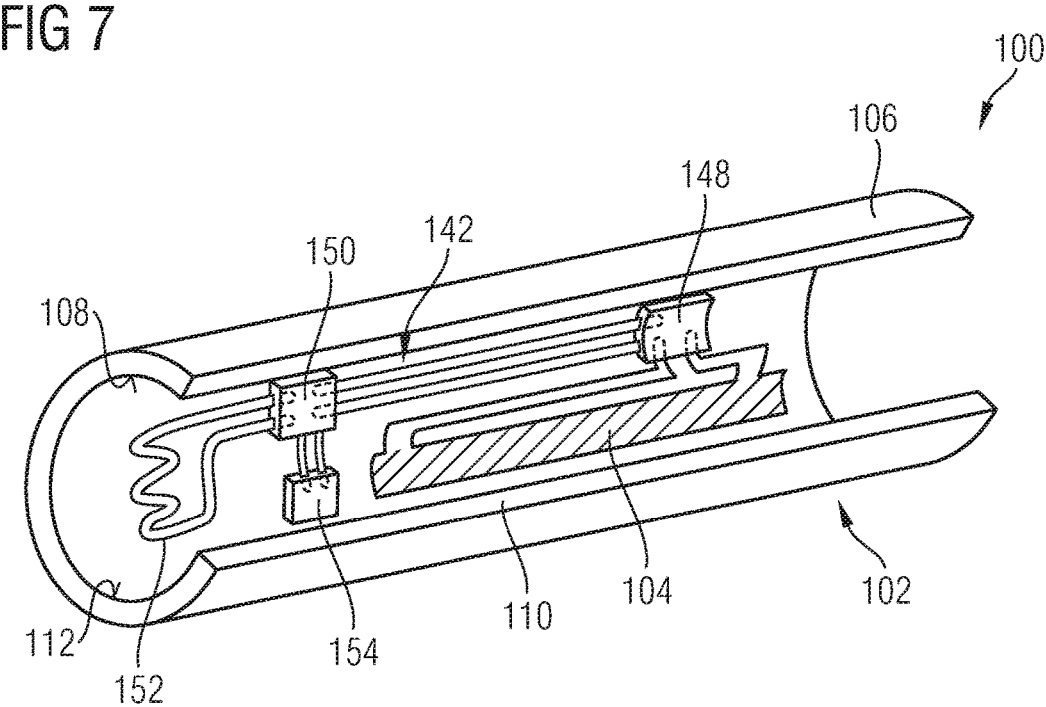
FIG. 7 is a schematic perspective view of an implantable device comprising an electrical circuitry according to an embodiment.

FIG. 7 is a schematic perspective view of an implantable device 100 comprising an electrical circuitry 142 according to an embodiment. The electrical circuitry 142 comprises a energy harvesting unit 148 connected to the piezoelectric part 104 of the implantable device 100. The energy harvesting unit 148 is adapted to convert the varying voltage of the piezoelectric part 104 into electric energy. The energy harvesting unit 148 is electrically connected to a transceiver unit 150, which includes an antenna unit 152 such as an antenna structure or an inductive structure. The transceiver unit 150 may comprise at least one of a radio frequency identification (RFID)/near field communication (NFC) antenna communicating with an external reader. RFID devices operate to different radio frequency ranges, e.g. low frequency (LF) at about 28 to 135 kHz, high frequency (HF) at about 13.56 MHz, and ultra-high frequency (UHF) at 860 to 960 MHz. In addition, communication may be performed via any one of an industrial, scientific and medical (ISM) band, which operates in a frequency range between 6.765 MHz to 246 GHz and has bandwidths of up to 2 GHz.

The implantable device 100 may further comprise a sensor unit 154 being connected to the transceiver unit 150 for transmitting a measurement result to the transceiver unit 150. The sensor unit 154 may comprise at least one of a pressure sensor, a flow sensor, a temperature sensor, an acceleration sensor, a gyro sensor or a magnetic sensor. The sensor unit 154 may further comprise components on, in or embedded into the body part 102 comprising microchannels for transport of fluidics for biochemical analytics purposes. Thus, the implantable device 100 may operate like a lab-on-a-chip device. The electrical circuitry 142 may comprise at least one of a transmitter, a receiver, a processor, a memory, or a power supply. The implantable device 100 may act as an independent sensor node. The sensor unit 154 probes a physical or chemical quantity and transmits it to the transceiver unit 150, which transmits the data to the outside of a human body or animal body. The necessary energy may be provided by external electromagnetic radiation (in which the antenna unit 152 may be used), by a battery or the energy harvesting unit 148.

As can be seen from FIG. 7, the cuff-formed implantable device has an open tube structure. This open tube may be flexible so that it can optionally be applied from the outside of the pulsatile tissue or a respective passage/conduit in a human or animal body by wrapping the first grasping part 106 and the second grasping part 110 around the pulsatile tissue 10. According to an embodiment, the body part 102 exhibits spring properties so that its open side can be reversely widened, as discussed above. By distorting the piezoelectric part 104, e.g. by periodic pressure change in a blood vessel or the pulsatile tissue 10, a periodic electrical voltage is created, which may be harvested by the energy harvesting unit 148 or may be measured for determining a pulse frequency, for example, or to measure periodic mechanical impact.

Figure 8:
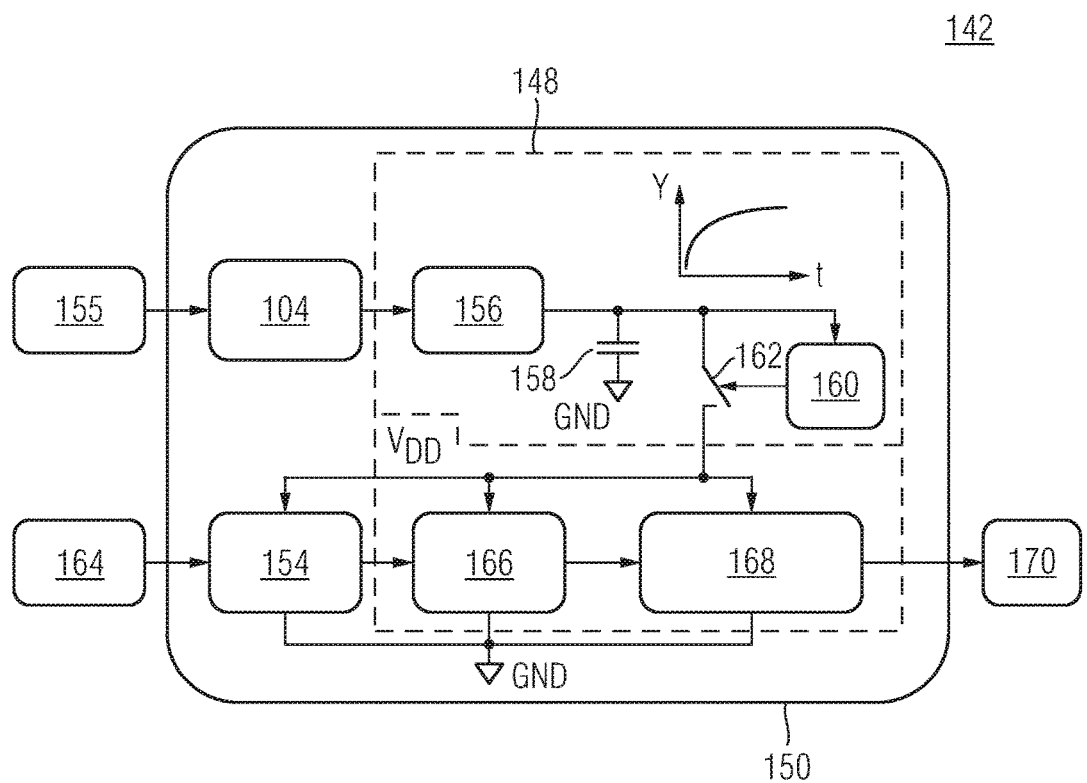
FIG. 8 is schematic circuit diagram of an electrical circuitry of an implantable device according to an embodiment.

A schematic circuit diagram of an electrical circuitry 142 of an implantable device 100 according to an embodiment is shown in FIG. 8. The electrical circuitry 142 comprises the sensor unit 154, the piezoelectric part 104, the energy harvesting unit 148 and the transceiver unit 150. The piezoelectric part 104 may comprise a piezoelectric material. The piezoelectric material may comprise polyvinylidene fluoride (PVDF). This material has a low Young's modulus (around 3 NPa), lacks hazardous materials (such as lead in PZT), and is formed in very thin sheets. However, any piezoelectric material may be used. Since the piezoelectric part 104 is interconnected between the first grasping part 106 and the second grasping part 110, the thickness of the piezoelectric part 104 may be the same as that of the body part 102.

As can be seen from FIG. 8, the pulsatile nature of arterial expansion and contraction 155 results in a low-frequency ambient biological energy source from which energy can be harvested by the piezoelectric part 104 and the energy harvesting unit 148, in order to provide autonomous power. The energy harvesting unit 148 includes an AC-to-DC converter 156, an energy storage unit 158, a level detection circuitry 160, and an electronic switch 162 to energize the rest of the electrical circuitry 142 when enough energy has been harvested. By this energy, sufficient power may be provided to complete a full operational cycle of the implantable device 100, such as a measurement process of the sensor unit 154 of a parameter of the pulsatile tissue 10 such as a blood pressure, a blood sugar concentration or a heparin concentration of blood in a vessel, a data storage process and, if called for in the particular cycle, a data transmission. All the components are optimized to achieve high energy-harvesting efficiency, minimal power loss, and very low leakage. The arterial expansion and contraction 155 is converted by the piezoelectric part 104 into a varying electrical voltage. The transceiver unit 150 comprises a data storage unit 166 and a communication unit 168 to transmit measurement data 170 to an external reader. The energy storage unit 158 may comprise a chargeable storage device. Herein, a silicon-based rechargeable lithium battery may be used. As silicon has highest lithium ion storage capacity/volume, even a very tiny-sized battery (A<1 mm$^2$) may provide storage capacity in the order of up to 250 to 500 µAh, which is sufficient for various applications. The energy storage unit 158 may further comprise a capacitor. Herein, printed energy storage devices or printed supercapacitors may be used.

Thus, measurement data of a parameter of a pulsatile tissue 10 or ambient fluid may be measured by the sensor unit 154, and the measurement data 170 may be transferred to an external reader, wherein the measurement and transmission process is energized by the energy harvesting unit 148 harvesting the pulsatile motion of the pulsatile tissue 10.

Figure 9:
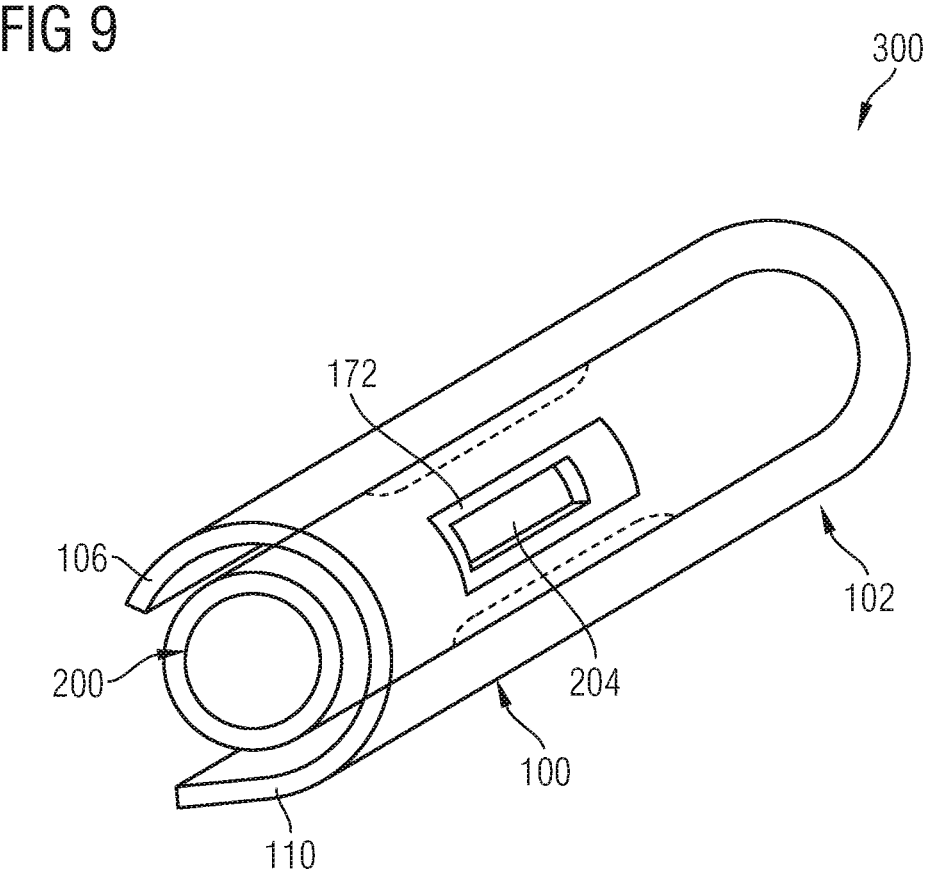
FIG. 9 is a schematic perspective view of an implantable system according to an embodiment.
Figure 10:
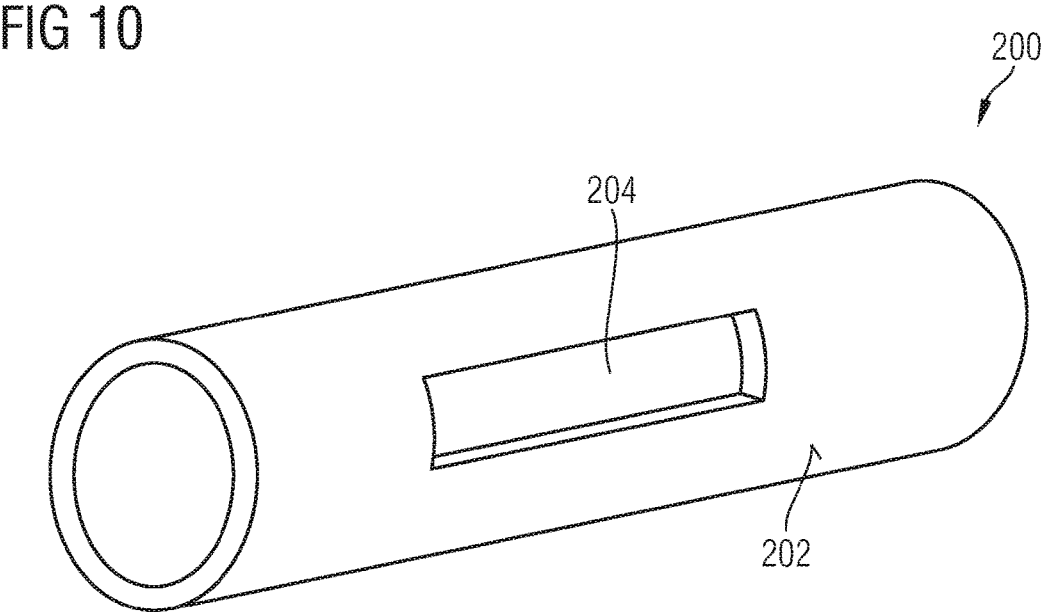
FIG. 10 is a schematic perspective view of a stent of an implantable system according to an embodiment.
Figure 11:
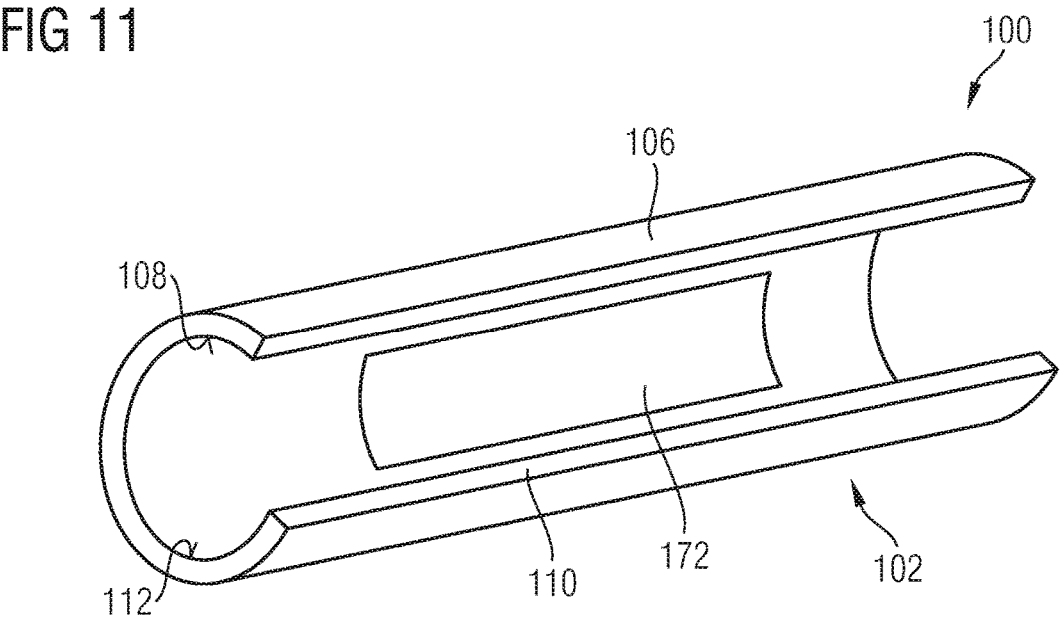
FIG. 11 is a schematic perspective view of an implantable device of an implantable system according to an embodiment.

FIG. 9 is a schematic perspective view of an implantable system 300 according to an embodiment. FIG. 10 is a schematic perspective view of a stent 200 of an implantable system 300 according to an embodiment. FIG. 11 is a schematic perspective view of an implantable device 100 of the implantable system 300 according to an embodiment.

As can be seen from FIGS. 9 to 11, the stent 200 comprises, according to an embodiment, an opening portion 204 in the circumferential surface 202 to provide access to an inner part of the pulsatile tissue 10. The implantable device 100 may comprise a sensor area 172, in which the sensor unit 154 may be located, which is located opposite to the opening portion 204 of the stent 200. The sensor area 172 may be adapted to measure a tissue fluid parameter e.g. pressure, flow velocity, or blood sugar of the inner part of the pulsatile tissue 10. Thus, the stent 200 inside the pulsatile tissue 10, e.g. a blood vessel, plastic tube, can be combined with the implantable device 100 being embedded as an outside open stent. Herein, the inner stent 200 can keep the pulsatile tissue 10, i.e. the vessel open for a blood flow while the implantable device 100 acting as an outer stent can be clamped around the pulsatile tissue 10, which may be a vessel, in order to position a functional element like the sensor unit 154 and connect it to outside systems, e.g. via printed wires on the surface of the outside stent surface of the implantable device 100 or the implantable device 100 itself. The functional element such as the sensor unit 154 in the sensor area 172 may incubate the pulsatile tissue such as the blood vessel through the opening portion 204 of the inner stent 200 and the pulsatile tissue 10 itself. The outer implantable device 100 is clamped over the pulsatile tissue 10 and seals the opening that was used to insert the inner stent 200 and allows to get the functional element such as the sensor unit 154 inside the blood stream of the pulsatile tissue 10.

In order to improve the sealing, a biocompatible glue may be used. In another embodiment, the electrical circuitry 142 may be connected to the inner stent 200 and the coupling between the inner stent 200 and the outer implantable device 100 may work via printed coils on either the stent 200 and the implantable device 100 that are arranged to form a transformer (inductive near field coupling). Thus, according to an embodiment, a tube-like structure for implantation into or around natural passages/conduits inside an animal or human body is provided, wherein the tube may contain electrical functions such as sensors or transceivers. Furthermore, the tube may be open and contain a piezo structure such as the piezoelectric part 104.

According to an embodiment, a functionalized stent is provided, which provides sensor data to an external reader. The pulsatile tissue 10 may be a blood vessel near to the heart region to apply the implantable device 100 as a cardiac pacemaker. However, the implantable device 100 may also be applied at other blood vessel regions to provide local energy harvesting in body regions like in a knee region or a leg region. Herein, also muscle energy may be harvested by the piezoelectric part 104 of the implantable device 100. The mechanical energy harvesting of the deformation of the blood vessels may be used to generate electric energy. From the intensity and frequency of the contraction and expansion process of the blood vessel, simultaneously blood pressure and pulse frequency may be measured, respectively.

FIGS. 12A to 12D are schematic perspective views of the stent 200 according to further different embodiments. The stent 200 discussed in the following may be employed in the implantable system 300 as discussed above. However, the stent 200 may not employed in the implantable system 300 but used alone. Furthermore, the stent discussed in the following may have the functionality as described above with regard to the implantable device 100.

The point-of-care (POC) technology for health care already makes inroads into our life. Various simple biological rapid tests are available on the market, such as blood glucose testing, pregnancy testing, and hemoglobin diagnostics. These tests are fast, low-cost, effective and simple. However the diagnostic of life-threatening infections and complex illnesses such as sepsis and cancer is still done by laboratories. If there is a serious illness suspicion, specialists need to analyze blood or tissue samples with time consuming and expensive procedures.

Highly miniaturized sensor grains or micro labs may be employed for amperometric measurements with biochips, impedance spectroscopy, or even deoxyribonucleic acid (DNA) detection using complementary metal oxide semiconductor (CMOS) sensor arrays. According to an embodiment, small wireless diagnostic devices may be directly implanted into a blood vessel. Thus blood parameter, such as blood glucose, can be measured instantly.

One of possible medical intensive treatments of an infarction is performed by means of catheter dilatation and stent implantation. The stent implantation is a well-established method to create space in a tube-shaped passage, such as an artery. Note, that stents can be also applied to support the flow of urine between kidney and bladder. Furthermore it can be implemented in the bronchus to measure according parameters.

According to an embodiment, the stent 200 may be adapted to measure liquid (blood, urine, etc.) or gas (Concentrations of Oxygen and/or $CO_2$ for example) parameters. The stent 200 may be therefore equipped with small sensor grains. A sensor grain may be a fully operating monolithic, chip-scaled device being adapted to measure liquid and gas parameters with its sensing surface. Herein, an integrated on-chip antenna may allow wireless communication and power transfer.

As can be seen from FIG. 12A, the stent 200 may comprise a lattice structure, a grid structure, a mesh structure, or a sieve structure, in the following indicated as lattice structure 206, which provides the stent 200 with an elastic behaviour. The lattice structure 206 may comprise a synthetic material and/or a metal material. The stent 200 as shown in FIG. 12A may comprise a lattice structure 206 of metal having a diamond structure. However, as can be seen from FIG. 12B to 12D, the stent 200 may have a lattice structure 206 with different geometries.

Figure 13A:
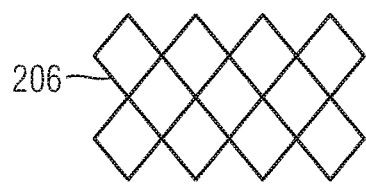
FIGS. 13A to 13H illustrate different lattice structures of a stent according to different embodiments.
Figure 13B:
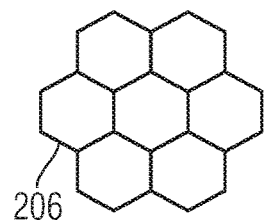
Figure 13C:
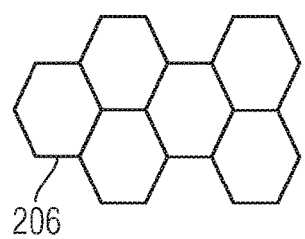
Figure 13D:
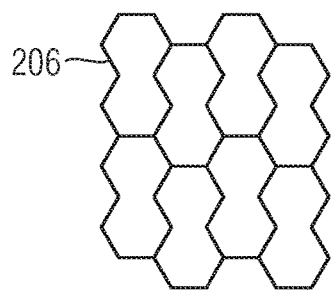
Figure 13E:
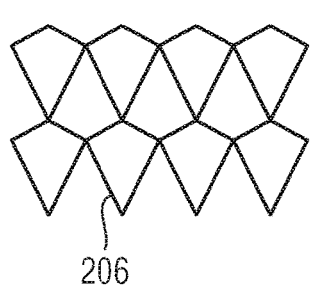
Figure 13F:
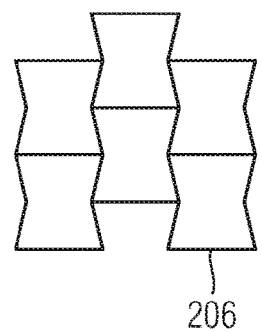
Figure 13G:
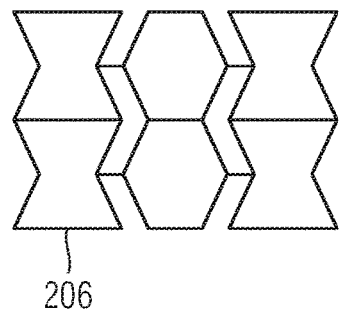
Figure 13H:
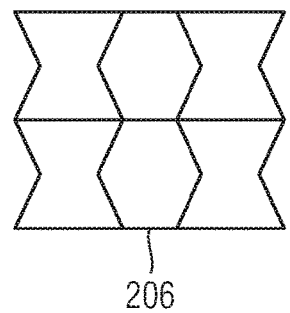

FIG. 13A to 13H show different lattice elements of lattice structures 206 according to different embodiments. Herein, FIG. 13A shows a diamond structure, FIG. 13B shows a hexagon A structure, FIG. 13C shows a hexagon B structure, FIG. 13D shows a double hexagon structure, FIG. 13E shows an arrow structure, FIG. 13F shows an auxetic structure, FIG. 13G shows an hybrid A structure, and FIG. 13H shows an hybrid C structure of a lattice structure 206.

FIGS. 14A and 14B illustrate different antenna structures of the stent 200 according to different embodiments.

FIG. 14A shows a portion of the lattice structure 206 of the stent 200 as shown, for example, in FIG. 12A to 12D. As can be seen from FIG. 14A, the lattice structure 206 may comprise a conductive lattice part 206a and a non-conductive lattice part 206b. The conductive lattice part 206a is illustrated as bolt lines, wherein the non-conductive lattice part 206b is illustrated as dashed lines.

In the embodiment of FIG. 14A, the conductive lattice part 206a is formed such that the conductive lattice part 206a has a structure of an electrically conductive coil. Herein, the ends of the conductive coil of the conductive lattice part 206 are connected with an electrical circuitry 208. The conductive lattice part 206a in FIG. 14A acts as a coil antenna structure 210 connected to the electrical circuitry 208. It shall be emphasized that the electrical circuitry 208 may have the same structure and the same functionality as the electrical circuitry 142 as shown in FIG. 5B, FIG. 6, FIG. 7 and FIG. 8. Herein, the coil antenna structure 210 of FIG. 14A may be employed as the inductive structure 144 or the antenna unit 152 as shown in FIG. 6 and FIG. 7.

To achieve the structure of the coil antenna 210, the conductive lattice part 206 of the lattice structure 206 of the stent 200 is formed such that parts of the conductive lattice part 206a are connected such that a closed loop of a conductive line is formed, wherein the conductive lattice part 206a is connected with the lattice structure 206 by the non-conductive lattice part 206b in such a way that the geometry of the lattice structure 206 is the same within the conductive lattice part 206a and the non-conductive lattice part 206b. In other words, the conductive lattice part 206a and the non-conductive lattice part 206b form together a lattice structure 206 without interruptions in the geometry or shape of the lattice structure. The conductive line of the conductive lattice part 206a may have a meander shape. The conductive part 206 may be formed by selectively coating a non-conductive material forming the non-conductive part 206b of the lattice structure 206 with a conductive material such as a metal, for example. In another embodiment, the lattice structure 206 may be formed as a composite structure formed of connecting the conductive lattice part 206a of a conductive material such as a metal and a the non-conductive part 206b of a non-conductive material such as a synthetic.

As can be seen from FIG. 14B, the conductive lattice part 206a may also be employed to form a dipole antenna 212. Herein, the conductive lattice part 206a comprises a first dipole antenna part 212a and a second dipole antenna part 212b each connected with a respective terminal of the electrical circuitry 208. As can be seen from FIG. 14B, the dipole antenna structure 212 is formed by providing closed areas of a conductive lattice part 206a surrounded by the non-conductive lattice part 206b.

The structure as shown in FIG. 14B may, for example, employed in an embodiment as shown in FIG. 5B, wherein the body part 102 of the implantable device 100 may be formed as the lattice structure 206 comprising the conductive lattice part 206a and the non-conductive lattice part 206b as shown in FIG. 14B.

Thus, as can be seen from FIG. 14A and FIG. 14B, both an inductive antenna structure and a dipole antenna structure may be provided by the stent 200 having the lattice structure 206 according to the embodiments of FIGS. 14A and 14B. Thus, it is possible to achieve antenna designs to perform a coil antenna 210 or a dipole antenna 212 within the lattice structure 206 of the stent 200.

Figure 15A:
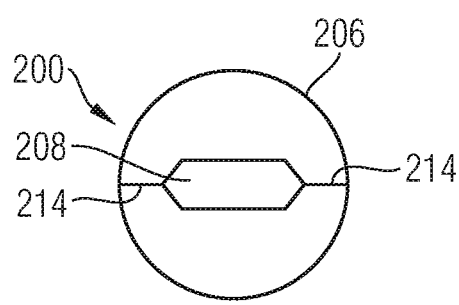
FIGS. 15A to 15C are schematic front and two side views of a stent comprising an electrical circuitry according to an embodiment, respectively.
Figure 15B:
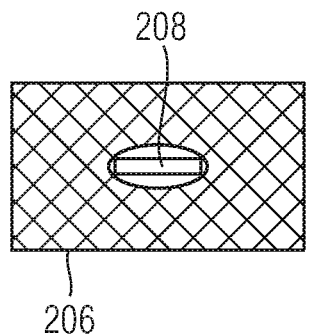
Figure 15C:
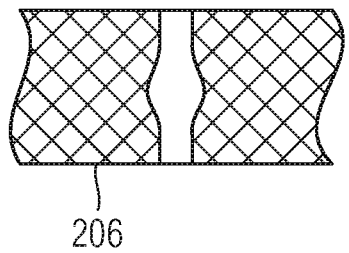

FIG. 15A to 15C are schematic front and two side views of the stent 200 comprising the electrical circuitry 208 according to an embodiment. As can be seen from FIG. 15A, the electrical circuitry 208 may be fixed to the lattice structure 206 of the stent 200 by fixing means 214. Herein the fixing means 214 hold the electrical circuitry 208 in a center position within the tubular lattice structure 206 of the stent 200. In the embodiment of FIG. 15A to 15C, the electrical circuitry 208 may be placed in the center of a vessel fluid current if deployed in a vessel 10 such as a blood vessel. Since the electrical circuitry 208 is placed in the center position of a vessel 10, a sensor area of the electrical circuitry 208 (as described, for example as the sensor unit 154 in FIG. 7 and FIG. 8) may be in contact with the vessel fluid flow. Thus, a good and reliable measurement result of the sensor unit 154 of the electrical circuitry 208 may be achieved.

Figure 16A:
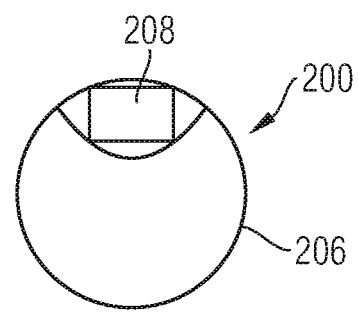
FIGS. 16A to 16C are schematic front and two different side views of a stent comprising an electrical circuitry according to another embodiment, respectively.
Figure 16B:
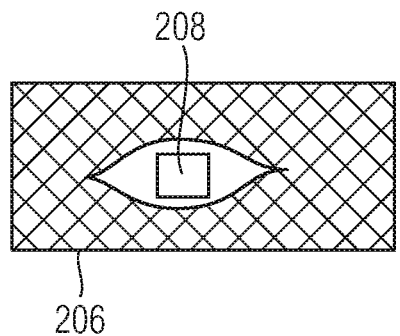
Figure 16C:
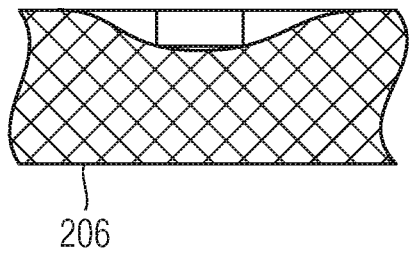

FIG. 16A to 16C are schematic front and two different side views of a stent 200 comprising an electrical circuitry 208 according to another embodiment.

According to this embodiment, the electrical circuitry 206 is fixed at an outer circumferential surface of the lattice structure 206 of the stent 200. The structure as shown in FIG. 16A provides the possibility to fix the electrical circuitry 208 at an outer portion of a blood vessel 10 if implanted into the same. By providing this structure, a disturbance of the blood vessel fluid flow in the vessel 10 by the electrical circuitry 208 is reduced in comparison to the structure as shown in FIG. 15A to 15C. Such an embodiment as shown in FIG. 16A to 16C may be employed in case the electrical circuitry 208 is used as a blood flow meter.

Figure 17A:
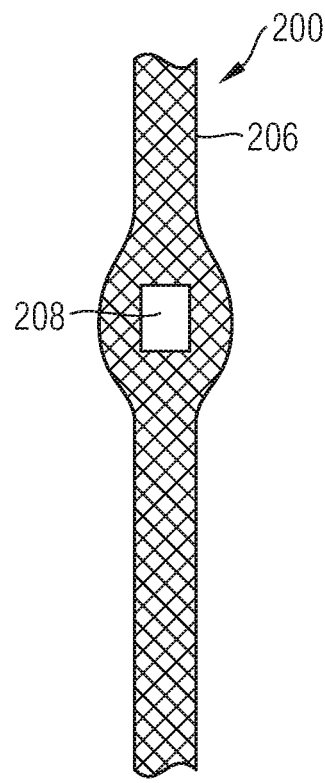
FIGS. 17A and 17B are schematic side views of a stent comprising an electrical circuitry according to an embodiment in a folded and a deployed state, respectively.
Figure 17B:
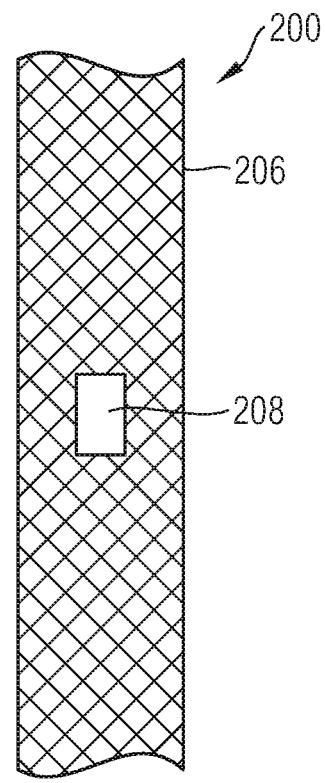

FIGS. 17A and 17B are schematic side views of a stent 200 comprising an electrical circuitry 208 according to an embodiment in a folded (or undeployed) (FIG. 17A) and a deployed (FIG. 17B) state.

Since the diameter of the lattice structure 206 in a folded state is much smaller than the diameter of the lattice structure 206 in a deployed state, the stent 200 may be positioned precisely within a particular location within a vessel 10. It further allows an easy/proven injection. In addition, it does not influence the vessel fluid flow, since the vessel 10 can be accordingly expanded.

Figure 18:
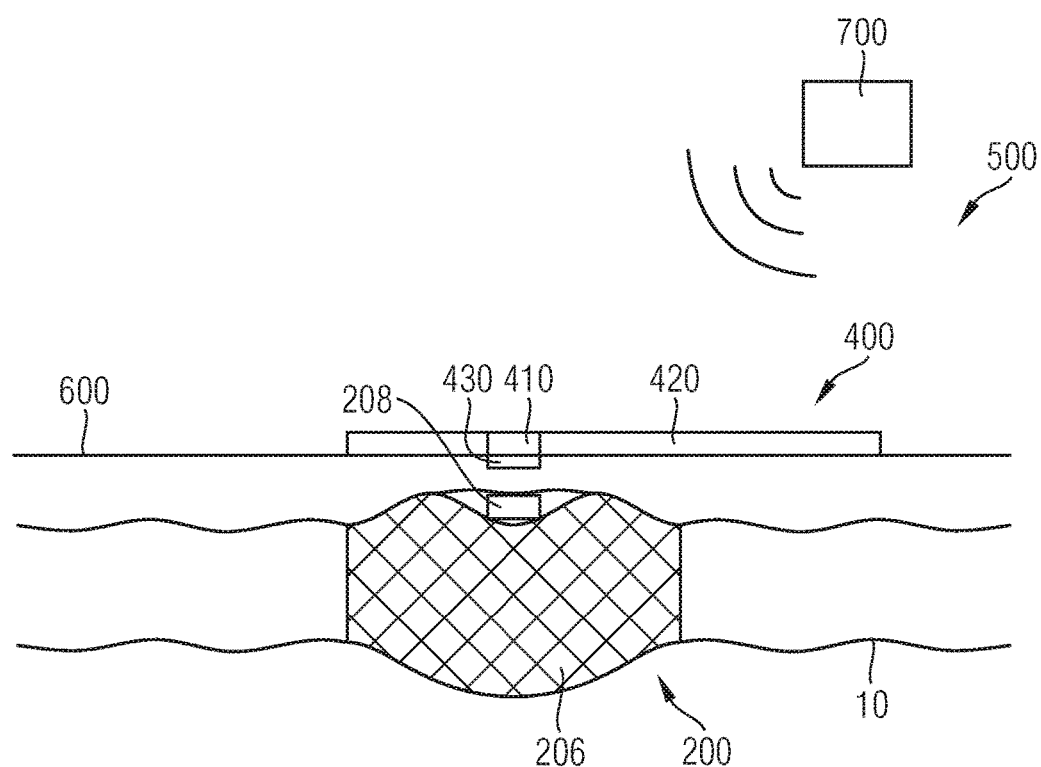
FIG. 18 is a schematic side view of a system comprising a stent and a booster device according to an embodiment.

FIG. 18 is a schematic side view of a system 500 comprising a stent 200 and a booster device 400 according to an embodiment. The booster device 400 comprises a booster antenna part 420 and an electrical circuitry 410 connected to the booster antenna 420. The booster device 400 further comprises a coupling antenna 430, which is adapted to communicate with an antenna structure of the stent 200 as shown in FIGS. 14A and 14B. The booster device 400 may be formed as a skin patch or a plaster to be attached to a skin 600 of a user.

The booster device 400 is adapted to receive electromagnetic waves from an external transceiver 700. The electromagnetic waves from the external transceiver 700 received by the booster antenna 420 are then guided to the electrical circuitry 410, which sends the electromagnetic waves from the external transceiver 700 to the antenna unit 152 (FIG. 7). The antenna unit 152 may be formed as a coil antenna 210 (FIG. 14A) or a dipole antenna 212 (FIG. 14B). The electromagnetic waves received by the antenna unit 152 are the guided to the electrical circuitry 208 of the stent 200.

Thus, a wireless communication between the external transceiver 700 with the electrical circuitry 208 of the stent 200 may be performed with support of the booster device 400. Herein, the booster device 400 may convert the communication frequency and may further boost the transmittance power to optimize the communication between the stent 200 and the external transceiver 700. Furthermore, the booster device 400 may be adapted to load an energy storage device of the electrical circuitry 208 by means of an inductive coupling between the coupling antenna 430 and a coil antenna 210 of the stent 200. Thus, the wireless communication channel of the implanted diagnostic device of the stent 200 may be further improved by the use of the booster device 400 having the booster antenna 420 and the coupling antenna 430.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An implantable device, comprising:
   a body part configured to grasp a pulsatile tissue when the device is implanted in said pulsatile tissue; and
   a piezoelectric part being mechanically coupled to the body part and configured to convert a varying shear force transferred from the body part to the piezoelectric part into voltage, wherein the body part comprises:
   a first grasping part being configured to grasp a first tissue part of the pulsatile tissue with a first surface area; and
   a second grasping part being configured to grasp a second tissue part of the pulsatile tissue with a second surface area, the first surface area and the second surface area facing each other,
   wherein the piezoelectric part is mechanically interconnected between the first grasping part and the second grasping part,
   wherein the first grasping part and the second grasping part comprise:
   a stiff part in a region directly adjoining the piezoelectric part; and
   an elastic part in a region directly adjoining the stiff part.

2. The implantable device of claim 1, wherein the body part and the piezoelectric part form a cuff configured to grasp the pulsatile tissue when the device is implanted in the tissue.

3. The implantable device of claim 1, wherein the body part and the piezoelectric part form a tube structure configured to enclose the pulsatile tissue.

4. The implantable device of claim 3, further comprising an additional piezoelectric part mechanically interconnected between the first grasping part and the second grasping part.

5. The implantable device of claim 1, wherein the body part comprises a piezoelectric material.

6. The implantable device of claim 1, wherein the first grasping part and the second grasping part are mechanically connected with each other by the interconnected piezoelectric part only.

7. The implantable device of claim 1, wherein the first grasping part and the second grasping part are mechanically connected with each other by the interconnected piezoelectric part and at least one end part comprising an elastic end part.

8. The implantable device of claim 1, wherein a region of the first grasping part and the second grasping part directly adjoining the piezoelectric part comprises a stiff material.

9. The implantable device of claim 1, wherein the stiff part and the elastic part comprise a synthetic material of the same material composition, the synthetic material being chemically hardened within the stiff part.

10. The implantable device of claim 1, wherein the stiff part and the elastic part comprise a synthetic material of the same material composition, the synthetic material being coated within the stiff part.

11. The implantable device of claim 1, further comprising an energy harvesting unit configured to convert the varying voltage of the piezoelectric part into electric energy.

12. The implantable device of claim 1, further comprising an antenna structure or an inductive structure coated on the surface of the body part by metal coating.

13. The implantable device of claim 1, further comprising an electrical circuitry comprising at least one of a transmitter, a receiver, a processor, a memory, or a power supply.

14. The implantable device of claim 1, further comprising a sensor unit comprising at least one of a pressure sensor, a flow sensor, a temperature sensor, an acceleration sensor, a gyro sensor, or a magnetic sensor.

15. The implantable device of claim 1, further comprising components on, in, or embedded into the body part comprising microchannels for transport of fluidics for biochemical analytics purposes.

16. An implantable system, comprising:
   an implantable device, comprising:

a body part configured to grasp a pulsatile tissue when the device is implanted in said pulsatile tissue; and a piezoelectric part being mechanically coupled to the body part and configured to convert a varying shear force transferred from the body part to the piezoelectric part into voltage, wherein the body part comprises:
- a first grasping part being configured to grasp a first tissue part of the pulsatile tissue with a first surface area; and
- a second grasping part being configured to grasp a second tissue part of the pulsatile tissue with a second surface area, the first surface area and the second surface area facing each other, wherein the piezoelectric part is mechanically interconnected between the first grasping part and the second grasping part, wherein the first grasping part and the second grasping part comprise:
- a stiff part in a region directly adjoining the piezoelectric part; and
- an elastic part in a region directly adjoining the stiff part; and a stent adapted to be inserted and deployed within the pulsatile tissue, the implantable device configured to form a sealed junction area with the pulsatile tissue while pressing against an outer circumferential area in an circumferential surface of the stent.

17. The implantable system of claim 16, wherein the stent comprises an opening portion in the circumferential surface to provide access to an inner part of the pulsatile tissue.

18. The implantable system of claim 17, wherein the implantable device comprises a sensor area located opposite to the opening portion of the stent, the sensor area being adapted to measure a tissue fluid or gas parameter of the inner part of the pulsatile tissue.

* * * * *